POINSETTIA PLANT

Filed April 17, 1970 3 Sheets-Sheet 1

INVENTOR
JOSEF HOLM
BY
Oberlin, Maky, Donnelly & Renner
ATTORNEYS

POINSETTIA PLANT

Filed April 17, 1970 3 Sheets-Sheet 2

INVENTOR
JOSEF HOLM
BY
Oberlin, Maky, Donnelly & Renner
ATTORNEYS

POINSETTIA PLANT

Filed April 17, 1970 3 Sheets-Sheet 3

INVENTOR
JOSEF HOLM
BY
Oberlin, Maky, Donnelly & Renner
ATTORNEYS

United States Patent Office

Plant Pat. 3,122
Patented Apr. 18, 1972

3,122
POINSETTIA PLANT

Josef Holm, Stokke, Norway, assignor to Mikkelsens Inc., Ashtabula, Ohio

Filed Apr. 17, 1970, Ser. No. 29,711
Int. Cl. A01h 5/00
U.S. Cl. Plt.—86 1 Claim The present invention relates to a new and distinct variety of poinsettia plant, botanically known as *Euphorbia pulcherrima,* which was discovered by me as a sport or mutation of the poinsettia variety Paul Mikkelsen (U.S. Plant Patent No. 2,328) in the flowering crop produced at the Gjennestad Gartnerskole, Stokke, Norway.

Figure 2:
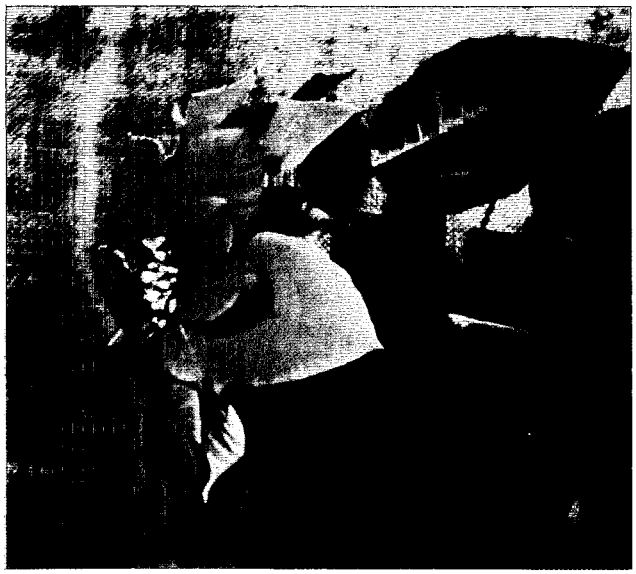

Young plants of the variety Paul Mikkelsen were purchased through the firm of Log. These young plants however were propagated by DCK in Sardenia, Italy, and were shipped to Oslo consigned to Log on behalf of the Gjennestad Gartnerskole. This was my first experience in growing the Paul Mikkelsen variety.

Late in the flowering season of the year these plants were purchased I noticed a particular plant that was not producing the proper type "stars" (bracts) on the top of the plants. The older foliage was very similar to the foliage of Paul Mikkelsen but the terminal foliage was less indented. There was a pronounced amount of lateral shoots which had imperfect stars near the base of this plant. Since this plant was different, it was labeled and saved for further experimental projects.

Cuttings were propagated from this plant during the spring and summer of the following year and present second generation stock was developed from these cuttings. Later in that year a considerable number of plants of my mutation were flowered in November and December along with the Paul Mikkelsen variety.

Twelve hundred (1200) plants of this mutation were flowered in the succeeding year, some as single stem, some stopped and branched some with self induced lateral shoots, and others as "splits." The mutation had similar bracts to Paul Mikkelsen but a brighter red color. The involucre of the mutation tended to cup upward. The veining of the leaves was more pronounced than on Paul Mikkelsen. The uppermost true leaves also developed more pigmentation than Paul Mikkelsen which enhanced the appearance of the mutation. The development of lateral shoots without removal of the terminal bud were more pronounced in cuttings propagated in July and August than in September. Very few plants developed side laterals when propagated in late September.

If plants of the mutation were "stopped" by removing the terminal bud in late August or September, a large number of side shoots developed. These all flowered with extreme symmetry, an economically significant factor in the floral industry.

If early cuttings of this mutation were produced from stock plants that were allowed to flower during the winter, "splits" would appear. This term is used in U.S. publications in describing plants of Paul Mikkelsen which prematurely initiate a flower bud that then aborts allowing terminal shoots to develop. The resulting shoots elongate causing a "split" flowering head but the involucre does not develop symmetrically. The involucre of my discovery, however, does develop symmetrically, a habit which is of economic significance to the floral industry.

Further appraisal of this mutation of Paul Mikkelsen disclosed that it also has the extremely good keeping qualities of the parent variety, maintaining its foliage and bracts up to six months and longer.

The cyathias of my discovery are very similar to the parent variety in size, color, and relative amounts of stamens and styles. It is noteworthy that this mutation has relatively the same proportion of multiple nectar cups as the parent variety. The pollen sacs appear to be smaller and appear to produce less pollen than the original parent variety. The retention of the cyathias on my mutation is improved over Paul Mikkelsen.

As previously mentioned, the color of the bracts is a brighter red on my mutation than on the original parent. In both cases there is twisting of the very terminal tip of the bracts as they mature.

The abundance of lateral growth of my mutation when the terminal tip is removed enhances the production of multiflowering plants and of cuttings for propagation. Although the stock plants become quite "grassy," thin cuttings from such stock plants root very rapidly and with a greater abundance of well diffused and heavier roots than Paul Mikkelsen.

Under controlled environmental conditions, single stem plants of my mutation have reached flowering in as little as seven weeks in the summer. The average time to flower under natural conditions in Norway is between eight and nine weeks. However multiple-flowering plants take seven to ten days more to reach the same stage of development as single stem plants.

Plants of my mutation are brought into flowering from October through the early part of the year by controlling daylength and temperatures as commonly practiced in the floriculture industry. Flowering is accomplished in the summer months by use of commonly practiced short day treatment techniques.

During the fall, winter, and spring months, my mutation is much slower growing variety than Paul Mikkelsen. It therefore does not generally need growth regulators to control height in the normal flowering season.

My new variety of poinsettia combines the following unique characteristics distinguishing it from other poinsettia varieties presently known to me:

(1) A short to medium height compact form that produces uniform and symmetrical multiflowering plants when "stopped" by removing the growing tip prior to flower initiation.

(2) A uniform and symmetrical plant when cuttings with "split" terminal buds are used.

(3) A variety that profusely produces cuttings which consistently propagate rapidly and with an abundance of strong roots.

(4) Consistently produced are bright red bracts with twisted tips, very similar to Paul Mikkelsen except for a slightly incurving involucre. Veining and pigmentation of the last true foliage on the peduncle is pronounced but varies in amounts, as does Paul Mikkelsen, depending on cultural practices employed to induce flowering and the development of the bracts.

(5) A long last variety that has good foliage placement, foliage with a sheen on well grown plants, and foliage with sufficient indentations and clean edges to be considered attractive.

(6) Self induced lateral branching is evident in early propagated cuttings but "stopped" plants are far more attractive. One single stem plant "stopped" may produce upwards of ten uniformly developed shoots.

(7) Rapid and uniform flowering response occurs in both single and multiple flowering type plants. Color enhancement is very rapid by lowering temperatures to 15 degrees centigrade near the end of the flowering period.

(8) The variety is very rugged.

Figure 1:
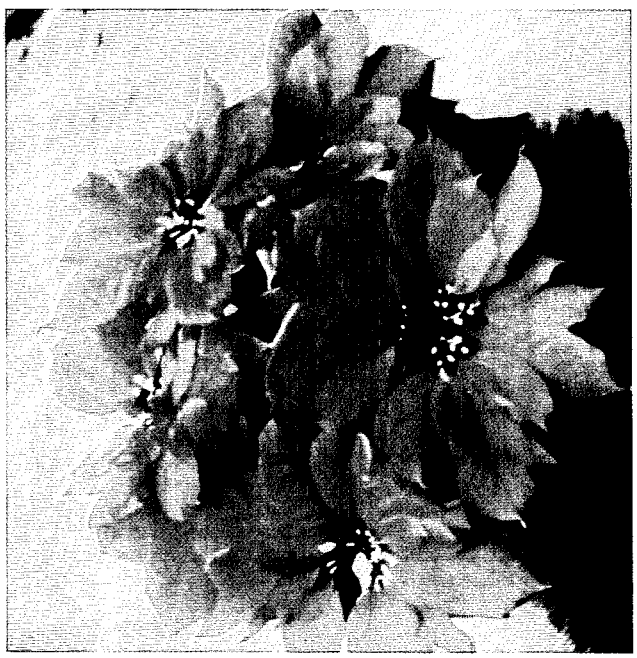
Figure 4:
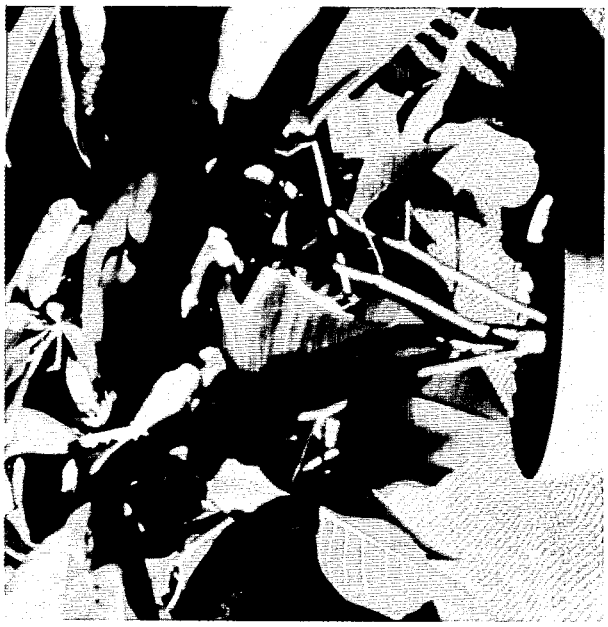
Figure 3:
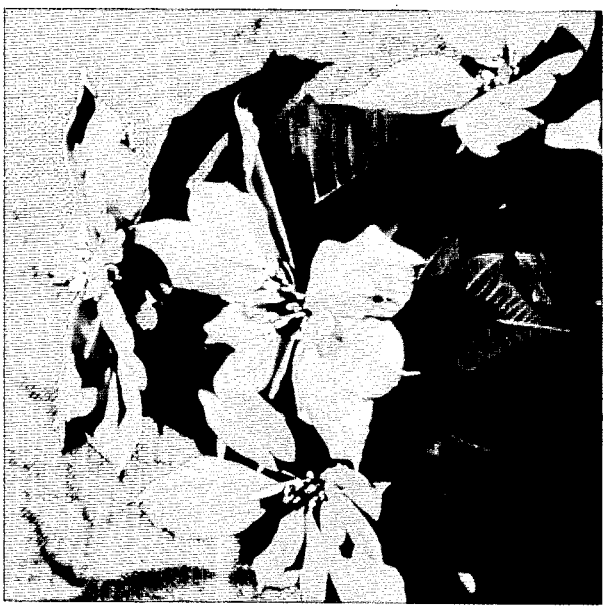
Figure 6:
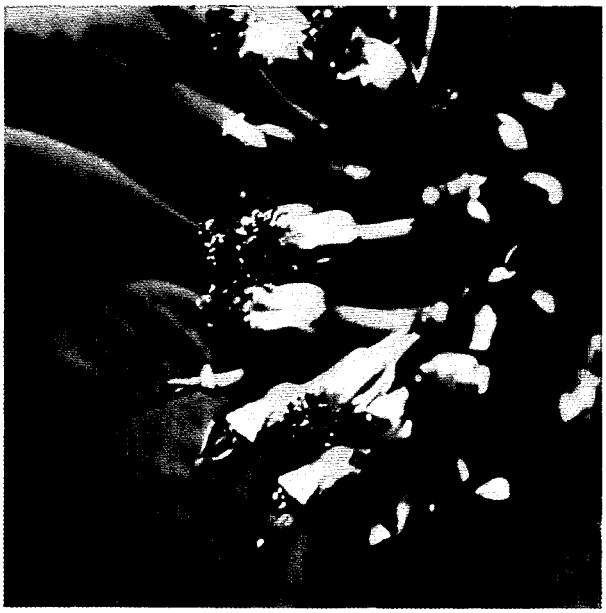
Figure 5:
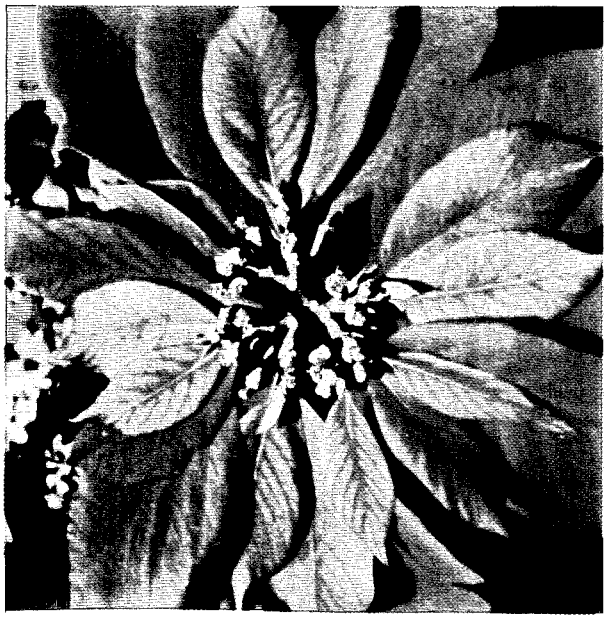

The accompanying drawings show specimens of my new poinsettia plant illustrated in color as true as reasonably possible, in which FIG. 1 is a view showing the number and placement of the bracts of a plurality of stems; FIG. 2 is a view showing a single stem; FIG. 3 is a view showing the self induced branching of the new variety; FIG. 4 is a view showing the multiple branching habit of the new variety; FIG. 5 is a close up view of the bracts and involucre, and FIG. 6 is a close up view of the cyathias.

The following is a detailed description of my new variety, with color terminology in accordance with the Royal Horticultural Society (R.H.S.) Colour Chart, except where general terms of ordinary dictionary significance are obvious, based on specimens grown in Stokke, Norway, under normal commercial fluoricultural practices.

Parentage: Mutation of the poinsettia variety Paul Mikkelsen (U.S. Plant Patent No. 2,328).

Form: Semi-draft, compact, upright with self induced branching possible under proper light and temperature conditions; and forced branching by removal of the terminal bud.

Habit of growth: Slower growing than the parent variety Paul Milkkelsen. When the terminal tip is removed, the abundance of side growth is much greater than normal, tending to slow down the over all rate of growth. There is some tendency to premature flower initiation, known as "splitting."

Rooting habit: Rooting is quite rapid, generally seven to ten days faster than Paul Mikkelsen. Roots are abundant, heavy, fibrous, and sturdy.

Blooming habit: Normal for poinsettias as to natural flowering season. This variety would be classed as an early flowering type. It flowers in as little as seven weeks in the summer. The involucre tends to be slightly incurved.

Blooming season: Late November under natural conditions in Stokke, Norway, with both day and night temperatures 20 degrees centigrade in the greenhouses during October, and 17–18 degrees centigrade in November. This variety may be forced earlier in the season by controlled day-length and forced later in the season by controlled night lighting.

Foliage: Alternate on peduncle at slight upward angle with exceptional retention after flowering maturity.

*Size.*—Varies considerably depending on the season of the year, being quite small on vegetative plants in the winter (5 cm. to 10 cm.) but getting as large as 10 cm. in width to 15 cm. in length in late spring and summer.

*Shape.*—Predominantly ovate (oak leaf) modifying to obovate under certain light conditions.

*Texture.*—Upperside becomes glossy at maturity; veins are recessed and dendritic and are quite pronounced. Underside—dull grey-green cast; veins are quite protruding and pronounced.

*Color.*—New foliage—upper side—in some seasons the newly developing foliage at the growing terminal starts as a yellow orange color, gradually turning predominately RHS 137B green during first mature stages. Underside—RHS 139C green.

Old foliage—upperside—RHS 139A green. Underside.—RHS 138B green.

Bracts: The last true leaves that tend to color and the very first true bracts tend to be plamate; secondary bracts tend to be broad obovate, and then modify to a narrower elliptical form as the involucre matures. Bracts continue to be retained on the flower stem and peduncle after cyathias drop. *Color.*—Upperside—at maturity is approximately RHS 44A red and fades in old age to RHS 45C red. Underside—RHS 50B red.

Flowers: (cyathia)

*Borne.*—Continuously for several months, with many flowers per stem in regular clusters in varying stages of development; borne on short and sturdy stems.

*Quality of bloom.*—Relatively abundant; continuous during one season of three or four months; cyathias gradually drop off after maturity, but new ones continue to develop as the flower stem continue to grow, the retention of the cyathias is superior to the Paul Mikkelsen.

*Flowering buds.*—Small; borne on light green stems the same color of the buds RHS 143B green. The total number of cyathia is comparable to those of the parent variety under similar growing conditions.

Reproductive parts:

*Stamens.*—Quite numerous; project from about 3 mm. to 6 mm. above the top of cyathia. Color, RHS 45D red.

*Pollen.*—Color, RHS 12 yellow. Pollen tends to mature and dry out more quickly then the pollen of Paul Mikkelsen.

*Styles.*—As numerous as in the parent variety and nearly the same size. Color, RHS 45A red.

*Ovaries.*—Color, RHS 143C green.

*Nectar cups.*—Usually occur singly but are sometimes double around the cyathia. Color, RHS 15A yellow.

I claim:

1. A new and distinct variety of poinsettia plant, substantially as herein shown and described, characterized as to novelty by the unique combination of a rapid and strong rooting habit, compact foliage of good color and texture, faster and easier flowering as single stem plants, a habit resulting in a large number of side shoots when stopped by removing the terminal bud, with these being flowered uniformly and symmetrically, a habit permitting the profuse production of cuttings which consistently propagate rapidly, a symmetrical involucre, attractive bright red bracts, rapid and uniform flowering in both single and multiple flowering plants, and long lasting and rugged plant qualities.

No references cited.

ROBERT E. BAGWILL, Primary Examiner

UNITED STATES PATENT OFFICE
CERTIFICATE OF CORRECTION

Patent No. Plant Patent 3122 Dated April 18, 1972

Inventor(s) JOSEF HOLM

It is certified that error appears in the above-identified patent and that said Letters Patent are hereby corrected as shown below:

In column 1, line 17, "Log" should be --LOG--.

In column 3, line 14, "semi-draft" should be --semi-dwarfed--.

In column 3, line 19, "Milkkelsen" should be --Mikkelsen--.

In column 4, line 4, "plamate" should be --palmate--.

Signed and sealed this 22nd day of August 1972.

(SEAL)
Attest:

EDWARD M.FLETCHER,JR.
Attesting Officer

ROBERT GOTTSCHALK
Commissioner of Patents